United States Patent [19]

Berg

[11] Patent Number: 5,332,478
[45] Date of Patent: Jul. 26, 1994

[54] SEPARATION OF 1-PROPANOL FROM 2-BUTANOL BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 180,969

[22] Filed: Jan. 14, 1994

[51] Int. Cl.$^5$ .............................................. B01D 3/36
[52] U.S. Cl. ...................................... 203/58; 203/60; 203/62; 203/63; 568/913
[58] Field of Search ....................... 203/60, 63, 62, 58; 568/913

[56] References Cited

U.S. PATENT DOCUMENTS

| | | | |
|---|---|---|---|
| 2,483,246 | 9/1949 | Stribley | 203/60 |
| 2,487,086 | 11/1949 | Amick et al. | 203/63 |
| 2,489,619 | 11/1949 | Carlson et al. | 203/63 |

*Primary Examiner*—Wilbur Bascomb, Jr.

[57] ABSTRACT

1-Propanol is difficult to separate from 2-butanol by conventional distillation or rectification because of the proximity of their boiling points. 1-Propanol can be readily separated from 2-butanol by azeotropic distillation. Effective agents are t-butyl methyl ether, 1,4-dioxane and ethyl formate.

1 Claim, No Drawings

SEPARATION OF 1-PROPANOL FROM 2-BUTANOL BY AZEOTROPIC DISTILLATION

FIELD OF THE INVENTION

This invention relates to a method for separating 1-propanol from 2-butanol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

There are a number of commercial processes which produce complex mixtures of oxygenated organic compounds, e.g. the Fischer-Tropsch process. In this mixture, a series of homologous alcohols are often produced. Two of the commonest alcohols in this mixture are 1-propanol and 2-butanol. 1-Propanol boils at 97.2° C. and 2-butanol at 99.5° C. The relative volatility between these two is 1.17 which makes it very difficult to separate them by conventional rectification. Azeotropic distillation would be an attractive method of effecting the separation of 1-propanol from 2-butanol if agents can be found that (1) will create a large apparent relative volatility between 1-propanol and 2-butanol and (2) are easy to recover from 1-propanol- Table 1 shows the relative volatility required to obtain 99% purity. With no agent, the relative volatility is 1.17 and 78 actual plates are required. With an agent giving a relative volatility of 1.65 only 25 plates are required.

OBJECTIVE OF THE INVENTION

The object of this invention is to provide a process or method of azeotropic distillation that will enhance the relative volatility of 1-propanol from 2-butanol in their separation in a rectification column. It is a further object of this invention to identify organic compounds which in addition to the above constraints, are stable, can be separated from 1-propanol and recycled to the azeotrope column with little decomposition.

TABLE 1

Theoretical and Actual Plates Required vs. Relative Volatility for 1-Propanol - 2-Butanol Separation

| Relative Volatility | Theoretical Plates Required At Total Reflux, 99% Purity | Actual Plates Required 75% Efficiency |
|---|---|---|
| 1.17 | 59 | 78 |
| 1.30 | 35 | 47 |
| 1.35 | 31 | 41 |
| 1.45 | 25 | 33 |
| 1.55 | 21 | 28 |

TABLE 1-continued

Theoretical and Actual Plates Required vs. Relative Volatility for 1-Propanol - 2-Butanol Separation

| Relative Volatility | Theoretical Plates Required At Total Reflux, 99% Purity | Actual Plates Required 75% Efficiency |
|---|---|---|
| 1.65 | 19 | 25 |

SUMMARY OF THE INVENTION

The objects of this invention are to provide a process for separating 1-propanol from 2-butanol which entails the use of certain organic compounds as the agent in azeotropic distillation.

DETAILED DESCRIPTION OF THE INVENTION

TABLE 2

Effective Azeotropic Distillation Agents For Separating 1-Propanol From 2-Butanol

| Compounds | Relative Volatility |
|---|---|
| None | 1.17 |
| Ethyl acetate | 1.3 |
| Isopropyl acetate | 1.25 |
| t-Butyl acetate | 1.3 |
| Isopropyl ether | 1.65 |
| t-Butyl methyl ether | 1.65 |
| Methyl ethyl ketone | 1.25 |
| Methyl isobutyl ketone | 1.4 |
| Methyl isopropyl ketone | 1.35 |
| Acetol | 1.25 |
| Propyl formate | 1.35 |
| 3,3-Dimethyl-2-butanone | 1.5 |
| 2,2-Dimethoxy propane | 1.4 |
| 1,4-Dioxane | 1.27 |
| Isobutyl acetate | 1.23 |
| Acetonitrile | 1.3 |
| Methyl formate | 1.3 |
| Ethyl formate | 1.35 |
| Ethyl ether | 1.55 |
| Tetrahydrofuran | 1.25 |
| Acetone | 1.25 |
| 3-Pentanone | 1.25 |
| 4-Methyl-2-pentanone | 1.4 |

I have discovered that certain organic compounds will greatly improve the relative volatility of 1-propanol to 2-butanol and permit the separation of 1-propanol from 2-butanol by rectification when employed as the agent in azeotropic distillation. Table 2 lists the compounds that I have found to be effective. They are ethyl acetate, isopropyl acetate, t-butyl acetate, isopropyl ether, t-butyl methyl ether, methyl ethyl ketone, methyl isobutyl ketone, methyl isopropyl ketone, acetol, propyl formate, ethyl formate, 2,2-dimethoxy propane, 1,4-dioxane, isobutyl acetate, acetonitrile, methyl formate, ethyl formate, ethyl ether, tetrahydrofuran, acetone, 3-pentanone, 4-methyl-2-pentanone and 3,3-dimethyl-2-butanone.

THE USEFULNESS OF THE INVENTION

The usefulness or utility of this invention can be demonstrated by referring to the data presented in Tables 1 and 2. All of the successful agents show that 1-propanol can be separated from 2-butanol by means of azeotropic distillation in a rectification column and that the ease of separation as measured by relative volatility is considerable.

WORKING EXAMPLES

Example 1

Sixty grams of 1-propanol, 40 grams of 2-butanol and 50 grams of t-butyl methyl ether were charged to a vapor-liquid equilibrium still and refluxed for three hours. Analysis indicated a vapor composition of 41.8% 1-propanol, 58.2% 2-butanol; a liquid composition of 30.3% 1-propanol, 69.7% 2-butanol. This is a relative volatility of 1.62.

Example 2

One hundred grams of a mixture comprising 60% 1-propanol and 40% 2-butanol and 100 grams of 1,4-dioxane was placed in the stillpot of a 7.3 theoretical plate glass perforated plate rectification column and refluxed for four hours. The overhead composition was 86.7% 1-propanol, 13.3% 2-butanol; the bottoms composition was 53.2% 1-propanol, 46.8% 2-butanol which is a relative volatility of 1.27.

I claim:

1. A method for recovering 1-propanol from a mixture of 1-propanol and 2-butanol which comprises distilling a mixture of 1-propanol and 2-butanol in the presence of an azeotrope forming agent, recovering the 1-propanol and the azeotrope forming agent as overhead product and obtaining the 2-butanol as bottoms product, wherein said azeotrope forming agent consists of one material selected from the group consisting of ethyl acetate, isopropyl acetate, isobutyl acetate, t-butyl acetate, isopropyl ether, t-butyl methyl ether, ethyl ether, acetone, methyl ethyl ketone, methyl isobutyl ketone, methyl isopropyl ketone, 3-pentanone, 4-methyl-2-pentanone, 3,3-dimethyl-2-butanone, methyl formate, ethyl formate, propyl formate, acetol, 1,4-dioxane, 2,2-dimethoxy propane, acetonitrile and tetrahydrofuran.

* * * * *